(12) United States Patent
Ruane et al.

(10) Patent No.: US 8,729,134 B2
(45) Date of Patent: May 20, 2014

(54) ARYL DI-SUBSTITUTED PROPENONE COMPOUNDS

(75) Inventors: Michael Ruane, Ardross (AU); Tracey-Ann Dickens, Mosman Park (AU)

(73) Assignee: Heartlink Limited, Nedlands, Perth (AU)

( * ) Notice: Subject to any disclaimer, the term of this patent is extended or adjusted under 35 U.S.C. 154(b) by 192 days.

(21) Appl. No.: 13/128,816

(22) PCT Filed: Nov. 13, 2009

(86) PCT No.: PCT/AU2009/001483
§ 371 (c)(1),
(2), (4) Date: Jul. 15, 2011

(87) PCT Pub. No.: WO2010/054438
PCT Pub. Date: May 20, 2010

(65) Prior Publication Data
US 2011/0263721 A1    Oct. 27, 2011

(30) Foreign Application Priority Data
Nov. 14, 2008    (AU) ............................... 2008905925

(51) Int. Cl.
*A01N 35/00*    (2006.01)
*A61K 31/12*    (2006.01)
*C07C 49/00*    (2006.01)

(52) U.S. Cl.
USPC .......................................... 514/685; 568/331

(58) Field of Classification Search
USPC .......................................... 514/685; 568/331
See application file for complete search history.

(56) References Cited

U.S. PATENT DOCUMENTS 7,612,114 B2    11/2009    Hamaoka et al.

FOREIGN PATENT DOCUMENTS

| WO | WO93/10741  | 6/1993  |
| WO | WO98/08503  | 3/1998  |
| WO | WO00/66575  | 11/2000 |
| WO | WO00/66576  | 11/2000 |
| WO | WO2004/058682 | 7/2004 |

OTHER PUBLICATIONS

King et. al., Journal of the Chemical Society, 1952, Chemical Society, pp. 1920-1924.*
Cole et. al., Journal of Medicinal Chemistry, 2003, American Chemical Society, vol. 46, pp. 207-209.*
Okudaira et. al., The Journal of Pharmacology and Experimental Therapeutics, 2000, The American Society for Pharmacology and Experimental Therapeutics, vol. 294, No. 2, pp. 580-587.*
Hong, Sung Joon, et al., "Comparative Study of Concentration of Isoflavones and Lignans in Plasma and Prostatic Tissues of Normal Control and Benign Prostatic Hyperplasia", 2002, Yonsei Medical Journal, vol. 43, No. 2, pp. 236-241.
Mosmann, Tim, "Rapid Colorimetric Assay for Cellular Growth and Survival: Application of Proliferation and Cytotoxicity Assays", 1983, Journal of Immunological Methods, vol. 65, pp. 55-63.
Supplementary European search report from related EP 09 82 5656 dated Apr. 11, 2012, 9 pages.
Database Reaxys [Online] Elsevier; 1981, Bezuidenhoudt et al: XP002672011, J. Chem. Soc., pp. 263-269.
Sanmartin et al., "A convenient alternative route to .beta.-aminoketones", Tetrahedron Letters, vol. 50, No. 7, Jan. 1, 1994, pp. 2255-2264.
Database CA [Online] Chemical Abstracts Service, 1976, Fitzgerald et al., "Phytochemical examination of *Pericopsis* species", XP002672013, Journal of the Chemical Society, pp. 186-191.
Database CA [Online] Chemical Abstracts Service, 1953, King et al., "Chemistry of extractives from hardwoods. VII. Constituents of muninga, the heartwood of *Pterocarpus angolensis*. B. 2, 4-Dihydroxyphenyl 1-p-methoxyphenylethyl ketone (angolensin).", XP002672014, Journal of Chemical Society, ISSN: 0368-1769, 5 pages.
International Search Report for PCT/AU2009/001483, completed Mar. 12, 2010.
Notification of Transmittal of International Preliminary Report on Patentability for PCT/AU2009/001483, completed Sep. 7, 2010.
Jain, A. C., et al., "A Facile Synthesis of α-Methyldesoxybenzoins Including Racemates of Natural Angolensin, 2-O-Methylangolensin & 4-O-Methylangolensin", Nov. 1988, Indian Journal of Chemistry, vol. 27B, pp. 985-988.
Jain, A. C., et al., "Some Novel Observations on Ethoxymethylation of 2-Hydroxy- and 2-Methoxyphenyl Benzyl Ketones: Isolation of α-Methylene- and α-Hydroxy- Methyl Derivatives", Jan. 1989, Indian Journal of Chemistry, vol. 28B, pp. 10-14.
Xiao, Zhu-Ping, et al., "Polyphenols Based on Isoflavones as Inhibitors of *Helicobacter pylori* Urease", 2007, Bioorganic & Medicinal Chemistry, No. 15, pp. 3703-3710.

* cited by examiner

*Primary Examiner* — Sarah Pihonak
(74) *Attorney, Agent, or Firm* — Barnes & Thornburg LLP

(57) ABSTRACT

Compounds of formula (I):

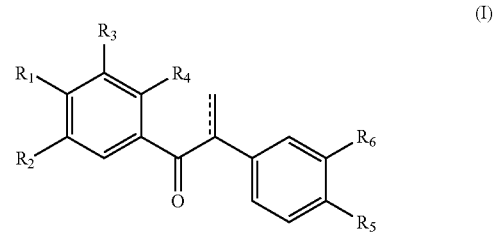

(I)

wherein $R_1$ and $R_4$ are $OR_7$, $R_2$ and $R_3$ are H or $OR_7$, with the proviso that when $R_2$ is $OR_7$ then $R_3$ is H, and when $R_3$ is $OR_7$ then $R_2$ is H; $R_5$ and $R_6$ are independently H, OH, or $OR_7$ with the proviso that when $R_5$ is OH, $R_6$ is not OH; $R_7$ is alkyl, aryl or arylalkyl; the drawing "====" represents either a single or a double bond; or pharmaceutically acceptable salt(s) or prodrug(s) thereof. These compounds are useful of treatment, prophylaxis, amelioration, or defense against and/or prevention of hormonal dependent conditions, cancer, and diseases and conditions associated with oxidant stress.

5 Claims, 3 Drawing Sheets

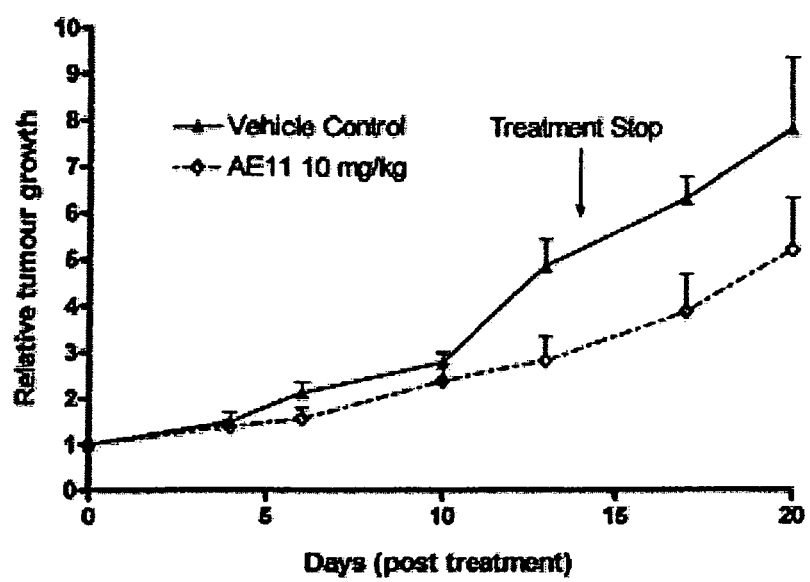
Figure 1 Treatment with AE11 at a dose of 10mg/kg significantly inhibits the growth of DU-145 prostate cancer tumours in mice.

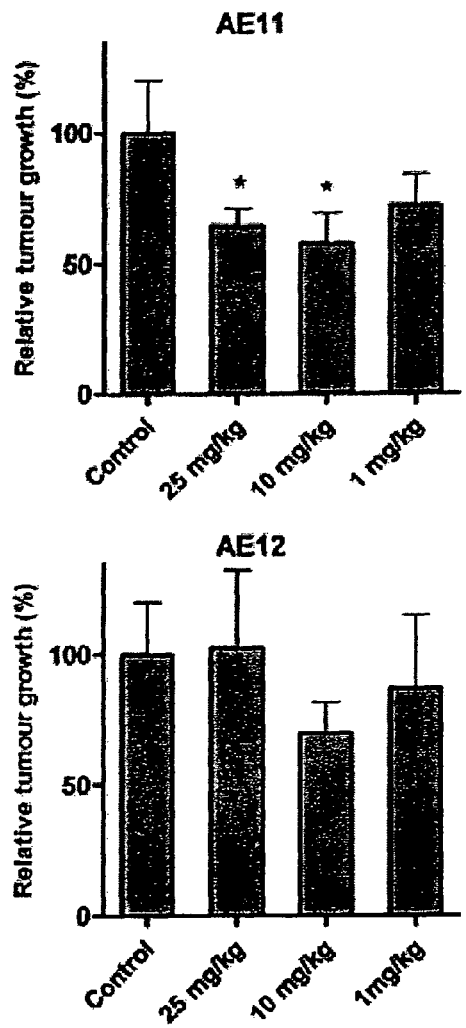

Figure 2. Growth inhibition of DU145 prostate cancer tumours after 14 days treatment with (A) AE11 and (B) AE12. Data shown is the percentage ratio of the mean growth for each treatment group relative to the vehicle control group. The tumour growth was calculated as a ratio of tumour volume to the starting tumour volume prior to treatment for each mouse. Tumour volume was calculated according to: $[W^2 \times L]/2$ mm$^3$. Data is presented as mean ± SE and statistical significance was determined by unpaired t-test ( * P<0.05)

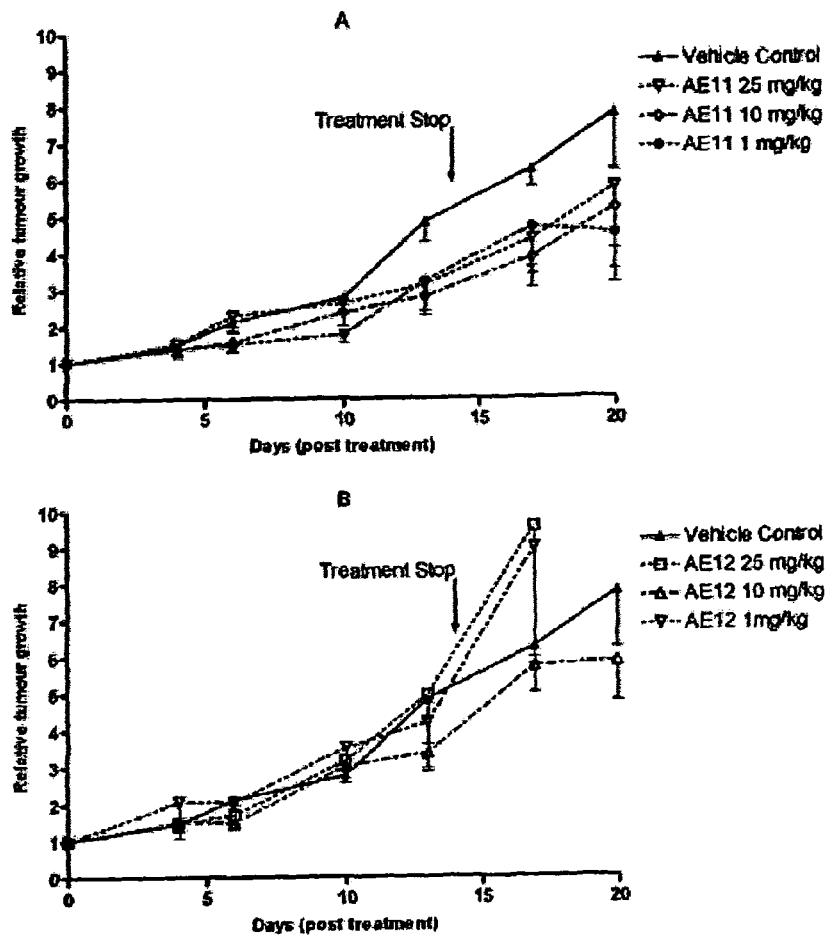

Figure 3 Treatment of DU145 prostate cancer tumours with (A) AE11 and (B) AE12. Data shown is the mean of the relative growth values for each surviving mouse in the treatment group. The relative tumour growth was calculated as a ratio of tumour volume to the starting tumour volume prior to treatment for each mouse. Tumour volume was calculated according to: $[W^2 \times L]/2$ mm$^3$.

ARYL DI-SUBSTITUTED PROPENONE COMPOUNDS

CROSS-REFERENCE TO RELATED APPLICATIONS

This application is the U.S. national phase of PCT/AU2009/001483 filed Nov. 13, 2009. PCT/AU2009/001483 claims priority to Australian patent application 2008905925 filed Nov. 14, 2008. The disclosures of both AU 2008905925 and PCT/AU2009/001483 are hereby incorporated herein by reference

FIELD OF THE INVENTION

The present invention relates to aryl di-substituted propenone compounds, compositions containing the aryl di-substituted propenone compounds, and therapeutic uses of aryl di-substituted propenone compounds or compositions thereof.

BACKGROUND OF THE INVENTION

Substituted propenone compounds have been investigated to a limited degree for their estrogenic properties and their potential as anti-carcinogenic, anti-fungal, anti-proliferative and anti-oxidant therapeutics.

These investigations have been adjunct to studies involving flavanoid and isoflavanoid compounds since substituted propanones and propenones are open ring structures possibly being precursors to or metabolites of flavones and isoflavones.

Flavanoid and isoflavanoid compounds are attracting increased attention as several are known to display significant estrogenic activity, as well as anti-carcinogenic, antifungal, antiproliferative properties and anti-oxidative effects.

It has been postulated that the estrogenic activity of isoflavanoid compounds results from the distinct similarities in structure, molecular weight and polarities to estrogens which enable them to bind to mammalian estrogen receptors.

Additionally, the benzopyran moiety of several isoflavonoids is structurally similar to the fused rings of estradiol, and hydroxyl groups are critically located enabling binding to estrogen receptor proteins. Accordingly, the plant-derived isoflavonoids are increasingly referred to as phytoestrogens.

Daidzein and genistein are naturally occurring isoflavanoid compounds which are known to readily bind to estrogen receptors. These compounds are poly hydroxy-substituted isoflavones which show estrogenic activity and anti-proliferative activity against a number of cancer cell lines. Their partially methylated pre-cursors, formononetin and biochanin A, are also naturally occurring isoflavones found in high concentrations in red clover. Both of these molecules, however, are considerably less effective than their hydroxyl homologues eg. daidzein and genistein, in binding to estrogen receptors and as anti-proliferative agents.

Recent investigation as reported in WO 00/66575 has shown that isoflavanoid compounds which demonstrate vicinal diol substitution show increased therapeutic activity over daidzein and genistein. The vicinal diol substitution may be afforded by 6,7-dihydroxy substitution in the benzopyran moiety of the isoflavonoid compounds or by 3',4'-dihydroxy substitution on the 3-phenyl substituent.

Investigations by Hong et al (2002) demonstrated significant anti-proliferative properties of 2-dehydro-0-demethyl angolensin, an apolyhydroxyisoflavone metabolite, against a number of human cancer cell lines. This study suggested that the growth inhibitory properties of certain isoflavones may be effected by metabolite products rather than the parent isoflavone itself.

This invention commenced as a study of flavonoid and isoflavonoid metabolites to confirm the results of earlier workers with the synthesis of poly hydroxyl phenyl propanones and propenones.

Counter intuitively, the inventor of this invention has discovered that fully or partially methoxylated and otherwise substituted aryl propen-1-ones afford enhanced estrogenic and antiproliferative activity relative to closed ring isoflavones and also relative to poly hydroxy propanones and propen-1-ones.

Furthermore, the synthetic pathways for obtaining the methoxy derivatives are simpler than their hydroxy analogues as there is no requirement for protecting groups, and their subsequent removal. The reduction in the number of synthetic steps also minimises potential contaminants, leading to more straightforward purification processes. The resultant compounds are readily characterised.

SUMMARY OF THE INVENTION

In one aspect, the invention features a compound of formula (I):

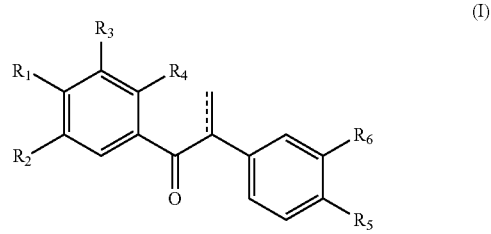

(I)

wherein $R_1$ and $R_4$ are $OR_7$; $R_2$ and $R_3$ are H or $OR_7$, with the proviso that when $R_2$ is $OR_7$ then $R_3$ is H, and when $R_3$ is $OR_7$ then $R_2$ is H;

$R_5$, $R_6$ are independently H, OH or $OR_7$, with the proviso that when $R_5$ is OH, $R_6$ is not OH;

$R_7$ is alkyl, aryl or arylalkyl;

the drawing " ------ " represents either a single or a double bond;

or pharmaceutically acceptable salt(s) or prodrug(s) thereof.

In another form, the invention relates to compounds of formula (IA):

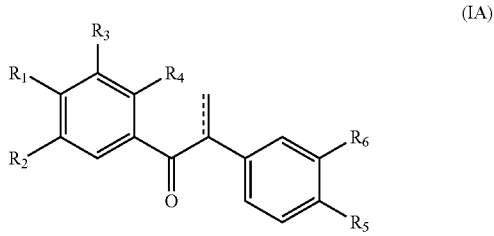

(IA)

wherein $R_1$ and $R_4$ are $OR_7$, $R_2$ is H, and $R_3$ is $OR_7$;

$R_5$, $R_6$ are independently H, OH or $OR_7$ with the proviso that when $R_5$ is OH, $R_6$ is not OH;

$R_7$ is alkyl, aryl, or arylalkyl;
the drawing "-----" represents either a single or a double bond.

In another form, the invention relates to compounds of formula (IB):

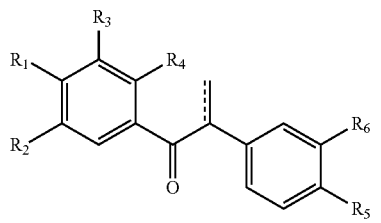

(IB)

wherein $R_1$ and $R_4$ are $OR_7$,
$R_3$ is H, and $R_2$ is $OR_7$;
$R_5$, $R_6$ are independently H, OH or $OR_7$ with the proviso that when $R_5$ is OH, $R_6$ is not OH.
$R_7$ is alkyl, aryl, or arylalkyl;
the drawing "-----" represents either a single or a double bond.

The term "alkyl" is taken to mean both straight chain and branched chain alkyl groups such as methyl, ethyl, propyl, isopropyl, butyl, isobutyl, secbutyl, tertiary butyl, and the like. The alkyl group has 1 to 10 carbon atoms, preferably from 1 to 6 carbon atoms, more preferably methyl, ethyl, propyl or isopropyl.

The term "aryl" is taken to include phenyl and naphthyl and may be optionally substituted by one or more $C_1$-$C_4$ alkyl, OH, or $C_1$-$C_4$ alkoxy.

Examples of preferred compounds of the invention are:
i) 1-(2,3,4-trimethoxyphenyl)-2-(4-methoxyphenyl)prop-2-en-1-one having the structure (II):

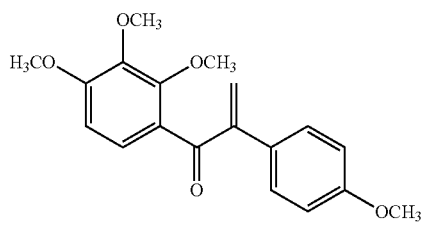

(II)

(hereinafter referred to as Compound II);
ii) 1-(2,4,5-trimethoxyphenyl)-2-(3,4-dimethoxyphenyl) prop-2-en-1-one having the structure (III):

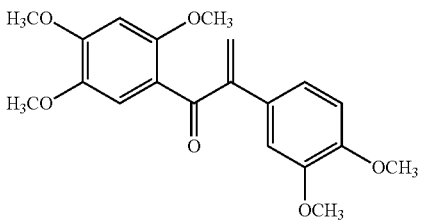

(III)

(hereinafter referred to as Compound III); and
iii) 1-(2,4-dimethoxyphenyl)-2-(3,4-dimethoxyphenyl) prop-2-en-1-one having the structure (IV)

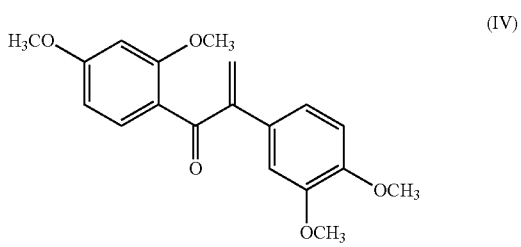 [SMILES: C=C(C(=O)c1ccc(OC)cc1OC)c1ccc(OC)c(OC)c1]

(IV)

(hereinafter referred to as Compound (IV)), or pharmaceutically acceptable salt(s) or prodrug(s) thereof.

A second aspect of the invention features a composition comprising one or more of the compounds of general formulae (I) as hereinabove defined, or a pharmaceutically acceptable salt or prodrug thereof, and one or more pharmaceutically, cosmetically or veterinarily acceptable vehicles, adjuvants, enhancers, diluents, and/or excipients.

The term "pharmaceutically, cosmetically or veterinarily acceptable" as used herein refers to pharmaceutically active agents, cosmetically active agents, veterinarily active agents, or inert ingredients which are suitable for use in contact with internal organs, live tissue, or the skin of human beings or animals without undue toxicity, incompatibility, instability, irritation, allergic response, and the like, commensurate with a reasonable benefit/risk ratio.

In a preferred embodiment of the invention, the composition comprises Compound II or a pharmaceutically acceptable salt or prodrug thereof and one or more pharmaceutically, cosmetically, or veterinarily acceptable vehicles, adjuvants, enhancers, diluents, and/or excipients.

In a third aspect of the invention, there is provided a food or drink composition containing one or more of the compounds of general formulae (I) as hereinabove defined, or a pharmaceutically acceptable salt or prodrug thereof. In one embodiment of the invention, the food or drink composition contains Compound II or a pharmaceutically acceptable salt or prodrug thereof.

In accordance with a fourth aspect of the invention there is provided a method for treatment, prophylaxis, amelioration, defence against and/or prevention of hormonal dependent conditions such as menopausal disorders including menopausal syndrome (hot flushes, anxiety, depression), mood swings, night sweats, premenstrual syndrome, fluid retention, dysmenorrhoea, cyclical mastalgia, headaches; osteoporosis; baldness including alopecia hereditaria; cardiovascular disorders including coronary artery spasm, myocardial infarction, stroke, atherosclerosis, hypertension vascular disease; all forms of cancer including breast cancer, uterine cancer, ovarian cancer, testicular cancer, large bowel cancer, endometrial cancer, prostatic cancer, leukeamia; and conditions such as benign prostatic hypertrophy; Reynaud's Syndrome; Buerger's Disease; migraine headache; Alzheimer's Disease; urinary incontinence; headaches; inflammatory diseases including inflammatory bowel disease ulcerative colitis, Chrohn's Disease, psoriasis; rheumatic disease including rheumatoid arthritis; acne; diseases associated with oxidant stress including cancer, arthritis; sunlight induced skin damage or cataracts, which method comprises administering to a subject a therapeutically effective amount of one or more of the compounds of general formulae (I) as hereinabove defined, or a pharmaceutically acceptable salt or prodrug thereof, either alone or in association with one or more pharmaceutically, cosmetically or veterinarily acceptable vehicles, adjuvants, enhancers, diluents, and/or excipients.

The term "effective amount" as used herein refers to an amount of composition sufficient to significantly induce an improvement in the condition that is treated, but low enough to avoid serious side effects. The effective amount of the composition will vary with the age and physical condition of the patient in need of treatment, the extent of the condition that requires treatment, the severity of the condition, the duration of the treatment, the particular pharmaceutically, cosmetically or veterinarily acceptable vehicle used, and like factors.

Preferably, Compound II or a pharmaceutically acceptable salt or prodrug thereof may be used in the method of treatment, prophylaxis, amelioration, defence against, and/or prevention of any one or more of the diseases described in the fourth aspect of the invention.

In a fifth aspect, the invention features the use of one or more compounds of general formulae (I) as hereinabove defined, or a pharmaceutically acceptable salt or prodrug thereof for the manufacture of a medicament for the treatment, prophylaxis, amelioration, defence against, and/or prevention of any one or more of the diseases described in the fourth aspect of the invention.

In accordance with a sixth aspect of the invention, there is provided use of one or more compounds of general formulae (I) as hereinabove defined, or a pharmaceutically acceptable salt or prodrug thereof for the treatment, prophylaxis, amelioration, defence against, and/or prevention of any one or more of the diseases described in the fourth aspect of the invention.

Preferably, Compound II or a pharmaceutically acceptable salt or prodrug thereof may be used in the fifth or sixth aspects of the invention.

BRIEF DESCRIPTION OF THE DRAWINGS

FIG. 1 is a graphical representation of relative growth of DU145 prostate cancer tumours in mice treated with Compound II at a dose of 10 mg/kg in comparison with mice treated with a vehicle control;

FIG. 2 is a graphical representation of growth inhibition of DU145 prostate cancer tumours after 14 days treatment with Compounds II and III at varying dosages; and, FIG. 3 is a graphical representation of growth inhibition of DU145 prostate cancer tumours after 14 days treatment with Compounds II and III at varying dosages.

DETAILED DESCRIPTION OF THE PREFERRED EMBODIMENTS

The invention features compounds of general formula (I):

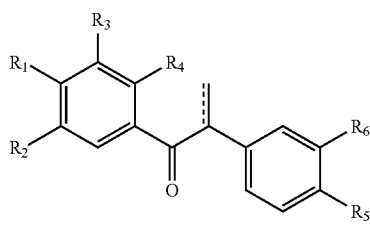

(I)

wherein $R_1$, and $R_4$ are $OR_7$; $R_2$ and $R_3$ are H or $OR_7$, with the proviso that when $R_2$ is $OR_7$ then $R_3$ is H, and when $R_3$ is $OR_7$ then $R_2$ is H;

$R_5$, $R_6$ are independently H, OH or $OR_7$ with the proviso that when $R_5$ is OH $R_6$ is not OH;

$R_7$ is alkyl, aryl or arylalkyl; the drawing "------" represents either a single or a double bond;

or pharmaceutically acceptable salt(s) or prodrug(s) thereof.

The compounds of the present invention may be obtained by chemical synthesis.

For example, one preferred compound of the invention is 1-(2,4-dimethoxyphenyl)-2-(3,4-dimethoxyphenyl)prop-2-en-1-one (Compound IV) which may be obtained according to the following reaction Scheme.

Synthesis of 1-(2,4-dimethoxyphenyl)-2-(3,4-dimethoxyphenyl)prop-2-en-1-one and similar compounds

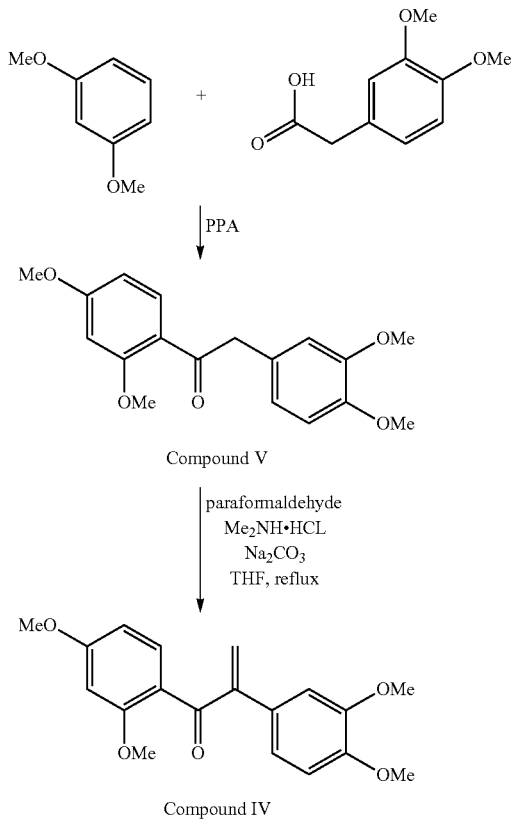

Compounds of the present invention have particular application in the treatment of diseases associated with or resulting from estrogenic effects, androgenic effects, vasodilatory and spasmodic effects, inflammatory effects and oxidative effects. In particular, the compounds of the present invention demonstrate significant anti-proliferative and cytotoxic effect against a range of tumour cell lines in culture.

The dosage of compounds in compositions formulated in accordance with the present invention will depend upon a number of factors, which include the specific application, the nature of the particular compound used, the condition being treated, the mode of administration, the route of administration and the condition of the patient. In general, a therapeutic daily dose per patient is in the range of 0.1 mg to 2 gm: typically from 0.5 mg to 1 gm: more typically 50 mg to 500 mg: preferably from 50 mg-250 mg.

The compositions of the invention are typically formulated for a form of administration including but not limited to oral, rectal, optical, buccal, parenteral, topical, and transdermal administration. The form of administration will be determined by a consideration of the nature and severity of the condition being treated and the nature of the compounds of the present invention used in the compositions.

Typically, one or more of the compounds of general formula (I), or a pharmaceutically acceptable salt or prodrug thereof is admixed with one or more pharmaceutically, cosmetically or veterinarily acceptable vehicles, adjuvants, enhancers, diluents, and/or excipients. The compositions may be prepared by means known in the art of preparing pharmaceutical, cosmetic, and/or veterinary compositions including blending, grinding, homogenizing, suspending, dissolving, emulsifying, dispersing, and where appropriate combining or mixing the compounds of the present invention with pharmaceutically, cosmetically or veterinarily acceptable vehicles, adjuvants, enhancers, diluents, and/or excipients.

The composition may be in a solid, semi-solid or liquid form. For example, the composition may be produced in a solid form in discrete units such as capsules or tablets, each discrete unit containing a predetermined amount of one or more of the compounds of the present invention, or as a powder or granules. The composition may be produced in liquid form as a solution, syrup, or suspension in aqueous or non aqueous media, or as a solution or suspension in an oil-in-water or water-in-oil emulsion. The composition may also be combined with a cosmetically acceptable vehicles for topical application in the form of an oil, lotion, creams, ointments, gels, paste, spray, aerosol, and solid formulations such as for example a wax-based stick. Other pharmaceutically, cosmetically, or veterinarily acceptable vehicles can be formulated by those of ordinary skill in the art.

Illustrative examples of formulations suitable for oral administration include but are not limited to capsules, cachets, lozenges or tablets, powders or granules, solution, syrup or suspension in an aqueous or non-aqueous liquid, solution or suspension as an oil-in-water emulsion or a water-in-oil emulsion. Each formulation is formulated to contain an effective amount of one or more of the compounds of the present invention.

The formulations for oral administration may be prepared by uniformly admixing the effective amount of one or more of the compounds with liquid or finely divided solid carrier or both, then, if required shaping the resultant mixture to form the required dosage unit. Orally administered formulations may generally contain up to 100% by weight of one or more of the compounds of the present invention.

Illustrative examples of formulations suitable for buccal administration include but are not limited to lozenges comprising an effective amount of one or more of the compounds of the present invention in a flavoured base such as sucrose, gum acacia or tragacanth with added flavouring agents such as peppermint oil, cherry, orange or raspberry flavourings; pastilles comprising an effective amount of one or more of the compounds of the present invention in an inert base such as gelatin, pectin or sucrose; chewing gum comprising an effective amount of one or more of the compounds of the present invention in a flavoured base of gum-base, fats and waxes.

Solid dose formulations intended for oral or buccal administration may contain pharmaceutically or veterinarily acceptable binders, sweeteners, disintegrating agents, diluents, coatings, preservatives, dispersants or delay release components. Examples of suitable binders include gum acacia, gum tragacanth, starch, carboxymethylcellulose and/or polyethelene glycol. Examples of suitable sweeteners include glucose, sucrose, aspartame or saccharine. Examples of suitable disintegrating agents include starch, agar, bentonite and methylcellulose. Examples of suitable diluents include sorbitol, lactose, kaolin, mannitol, cellulose and calcium silicate. Examples of suitable flavourings include peppermint oil, cherry, orange or raspberry flavourings. Examples of suitable coatings include methylacrylic acid and or esters, waxes and fatty alcohols. Examples of suitable preservatives include methyl paraben, propyl paraben, ascorbic acid and sodium bisulfite. Examples of suitable lubricants include magnesium stearate, sodium oleate, sodium chloride and talc. Examples of suitable time delay agents include glyeryl monostearate or di-stearate. Examples of suitable dispersing agents include lecithin, esters of fatty acids including stearic acid, polyoxyethylene sorbitol mono- or di-oleate and the like.

Illustrative examples of formulations suitable for parenteral administration comprises sterile aqueous preparations of an effective amount of one or more compounds of the present invention, and are preferably isotonic with the blood of intended recipient. The formulations may be administered intravenously, intraperitonealy, subcutaneous, intramuscular or by intradermal injection. The formulations may be prepared by admixing an effective amount of one or more compounds of the present invention with water or glycine buffer and rendering the resulting solution sterile and isotonic with blood.

Injectable formulations generally contain up to 80% w/v of an effective amount of one or more compounds of the present invention and are administered over a range of rates depending on administration route and condition. Examples of suitable non-toxic parenterally acceptable diluents or solvents include water, isotonic salt solutions, ethanol, propylene glycol or polyethylene glycols in mixtures, with or without buffering agents such as sodium acetate, sodium citrate, sodium borate for example.

Illustrative examples of formulations suitable for rectal administration are usually presented as unit dose suppositories, prepared by admixing an effective amount of one or more compounds of the present invention with a conventional solid carrier such as gelatin, waxes or cocoa butter and then shaping the resulting mix.

Illustrative examples of formulations suitable for topical application include but are not limited to ointment, cream, lotion, paste, gel, spray, aerosol or oil. Carriers may include cold cream base, lanolin, polyethylene glycols, alcohols, and petroleum jelly, singularly or in combination. The formulations typically include one or more compounds of the present invention present from 0.1% to 10% w/w.

Illustrative examples of formulations suitable for transdermal application include but are not limited to adhesive patches designed to remain in contact with the skin for prolonged periods. An effective amount of one or more compounds of the present invention is contained within a suitable proprietary matrix and may be buffered as required, together with proprietary permeation enhancers. The compounds of the present invention are generally present from 0.1M to 10M in the formulation.

The compounds of the present invention may also be administered via iontophoresis, following suitable buffering of the compound with citrate or bis/tris buffer (pH6) or ethanol/water. The compounds of the present invention are generally present from 0.1M to 10M in the formulation.

All of the above formulations may or may not be presented in a sterile form.

Alternatively, or additionally, the compounds of the present invention may be contained in foodstuffs, or provided in the form of foodstuffs, and may be added to, admixed into, coated, combined or otherwise added to a food stuff. The term "food stuff" as used herein is defined in the broadest terms and includes liquid formulations such as drinks, dairy products and other foods such as health drinks, health bars, sweet preparations and confections. Food stuff formulations can be prepared according to standard practice to those skilled in the art.

The compounds of the present invention have potent anti-oxidant activity and have applications in the pharmaceutical and veterinary fields, and in cosmetics. It is envisaged that the compounds of the present invention may be formulated into cosmetic formulations for use in therapeutic and/or cosmetic applications relating to anti-aging, moisturising, sunscreen, food, shampoo and hair care products, health products and such like.

Therapeutic methods, uses and compositions may be for administration to humans or animals (domestic, companion and livestock, including birds).

Preferred embodiments of the invention will now be more fully described with reference to the following examples.

EXAMPLE 1

Synthesis of 1-(2,4-dimethoxyphenyl)-2-(3,4-dimethoxyphenyl)ethanone (Compound V)

Warm polyphosphoric acid (100 g, 50° C.) was added to a warm suspension of 3,4-dimethoxyphenylacetic acid (7.46 g, 38.0 mmol, 60° C.) in 1,3-dimethoxybenzene (5.0 mL, 38.0 mmol). The resulting dark solution was stirred at 85° C. for 90 min then cooled to room temperature in a waterbath and water (150 mL) was added slowly to the solution.

The mixture was extracted with ethyl acetate (3×250 mL) and the combined organic extracts were washed with water (500 mL) and saturated brine (300 mL), then dried (anh. $MgSO_4$) and concentrated under reduced pressure to give an orange solid. Recrystallisation of the orange solid from methanol afforded Compound V (16.3 g, 51.5 mmol, 68%) as a yellow solid.

The recrystallisation mother liquor was evaporated to dryness to give a light brown solid which was recrystallized from methanol to give additional Compound V (3.22 g, 10.1 mmol, 13%) as a yellow solid.

NMR Data $^1$H NMR ($CDCl_3$, 7.26 ppm) δ 3.80 (3H, s); 3.85 (3H, s); 3.89 (3H, s); 3.91 (3H, s); 4.22 (2H, s); 6.45 (1H, d); 6.55 (1H, dd); 6.76 (3H, m); 7.80 (1H, d).

$^{13}$C NMR ($CDCl_3$, 78 ppm) δ 50.47, 56.40, 56.51, 56.74, 56.82, 99.33, 106.15, 112.04, 113.78, 122.66, 126.86, 129.37, 134.11, 148.60, 149.66, 161.58, 165.46, 199.06.

EXAMPLE 2

Synthesis of 1-(2,4-dimethoxyphenyl)-2-(3,4-dimethoxyphenyl)prop-2-en-1-one (Compound IV)

A mixture of Compound V (10.0 g, 31.6 mmol), paraformaldehyde (6.4 g), dimethylamine hydrochloride (9.4 g, 115 mmol) and sodium carbonate (13.3 g, 125 mmol) was dissolved in tetrahydrofuran (150 mL) and heated under reflux for 16 h. The reaction was cooled to room temperature, filtered and the filtrate was concentrated under reduced pressure to give a brown oil. Purification by column chromatography on silica gel 60, eluting with hexane/ethyl acetate (2:1 to 1:1) afforded Compound IV (5.3 g, 16 mmol, 51%) as a yellow oil.

Further elution afforded additional Compound IV together with a lower Rf component (2.1 g). Purification of this impure fraction by column chromatography on silica gel 60, eluting with hexane/ethyl acetate (3:1 to 1:1) afforded additional Compound V (0.84 g, 2.6 mmol) as a yellow oil.

NMR Data $^1$H NMR ($CDCl_3$, 7.26 ppm) δ 3.66 (3H, s); 3.79 (3H, s); 3.82 (3H, s); 3.84 (3H, s); 5.25 (1H, s); 5.57 (1H, s); 6.39 (1H, d); 6.49 (1H, dd); 6.80 (1H, d); 6.95 (2H, m); 7.60 (1H, d)

$^{13}$C NMR ($CDCl_3$, 77.01 ppm) δ 55.55, 55.59, 55.91, 55.94, 98.71, 104.86, 110.75, 110.92, 119.68, 120.12, 121.78, 130.46, 132.94, 148.58, 149.00, 150.60, 164.14, 196.19.

EXAMPLE 3

Activity of Compounds II-IV in Respect of Hormone Related Cancers

The activity of each of Compounds II-IV was investigated in respect to the treatment of hormone related cancers in vitro, including breast, ovarian, cervical, melanoma, myeloma and prostatic cancer.

Effects of Aryl Di-Substituted Propenone Compounds on the Induced Growth of Mammary Carcinoma Cells.

Compounds II-IV were compared with genistein to test the cell viability of MCF-7 cells (human, mammary, adenocarcinoma cell line) and MDA-MB-435 cells (human mammary ductal carcinoma). Genistein was known prior to this invention, to be the most potent individual inhibitor of cancer cells in in vitro experiments.

Cell viability was tested using the MTT assay (Amersham). The MTT [3-(4,5-dimethylthiazol-2-yl)-2,5-diphenyltetrazolium bromide] assay, was first described by Mosmann in 1983, (J Immunol Methods. 1983 Dec. 16; 65(1-2): 55-63). The assay is based on the ability of a mitochondrial dehydrogenase enzyme from viable cells to cleave the tetrazolium rings of the pale yellow MTT and form a dark blue formazan crystals which is largely impermeable to cell membranes, thus resulting in accumulation within healthy cells. Solubilisation of the cells by the addition of a detergent results in the liberation of the crystals which are then solubilized. The number of surviving cells is directly proportional to the level of the formazan product created. The colour can then be quantified using a simple colorimetric assay. The results can be read on a multi-well scanning spectrophotometer (ELISA reader).

Cells were plated at predetermined densities in 96 well plates. These were then incubated for 24 hours at 37° C. with 5%; $CO_2$. Growth medium was then removed and replaced with 100 μl of growth medium containing various dilutions of test reagents or appropriate controls.

Plates were then incubated for a either 48 or 96 hours.

MTT reagent was then added to each well. The plates were then incubated in a 37° C./5% $CO_2$ incubator. Detergent reagent was then added to each well. The plates were incubated overnight at 37° C./5% $CO_2$. The absorbance was read at 570 nm.

The results obtained with the MCF7 cells demonstrated that genistein showed an inhibition at 48 hours incubation with an IC50 of 79.4 μM, compared with IC 50 values of 2.2 μM for Compound II, 3 μM for Compound III, and 6.8 μM for Compound IV, for the same period.

Whilst with the MDA-MB-435 cell line results demonstrated that genistein showed an inhibition at 48 hours incubation with an IC50 of >100 µM, compared with IC 50 value of 0.6 µM for Compound II, 3.8 µM for Compound III, and 6.8 µM for Compound IV.

Effects of Aryl Di-Substituted Propenone Compounds on the Induced Growth of Prostate Carcinoma Cell Lines.

Compounds II-IV were compared with genistein to test the cell viability of LNCaP, PC3 and DU-145 cell lines (human prostate carcinoma).

The results obtained demonstrate that genistein showed inhibition of LNCaP cells at 48 hours incubation with an IC of 59.5µ, compared with IC 50 values of 2.3 µM for Compound II, 5 µM for Compound III and 6.1 µM for Compound IV. Compounds II-IV demonstrated inhibition in PC3 cells with IC 50 values of 2.7 µM, 8.6 µM, and 8.7 µM, respectively.

Genistein showed inhibition of DU-145 cells at 48 hours incubation with an IC 50 of 78.9 µM, compared with IC 50 values of 4.8 µM for Compound II, 15 µM for Compound III, and 10.7 for Compound IV.

Effects of Aryl Di-Substituted Propenone Compounds on the Induced Growth of Cervical and Ovarian Carcinoma Cells.

Compound IV was compared with genistein to test the cell viability of JAM (ovarian carcinoma) and HELA (human cervical carcinoma) cell lines.

The results obtained demonstrate that genistein showed inhibition of JAM cells at 96 hours incubation with an IC 50 of 9.7 mcg/ml. Compound V demonstrated inhibition with an IC 50 values of 0.9 mcg/ml (JAM) and 3 mcg/ml (HELA) at 96 hour incubation.

Compound IV is more potent as a cytotoxic agent than genistein on these cell lines.

Also, Compounds II-IV were compared with genistein to test the cell viability of SK-OV-3 (ovarian adenocarcinoma), OVCAR-3 (ovarian adenocarcinoma), and C-33A (cervical carcinoma) cell lines. Compounds II, III, and IV demonstrated inhibition in SK-OV-3 cells with IC 50 values of 21.5 µM, 33.1 µM, and 27.4 µM, respectively.

Compounds II, III, and IV demonstrated inhibition in OVCAR-3 cells with IC 50 values of 3.3 µM, 11.7 µM, and 16.9 µM, respectively.

Genistein showed inhibition of C-33A cells at 48 hours incubation with an IC 50 of 41.9 µM, compared with IC 50 values of 1.8 µM for Compound II, 3.1 µM for Compound III, and 2.4 µM for Compound IV.

Effects of Aryl Di-Substituted Propenone Compounds on the Induced Growth of Melanoma Cells.

Compound IV was compared with genistein to test the cell viability of B16-F1 cells (murine melanoma).

The results obtained demonstrate that genistein showed inhibition of B16-F1 cells at 96 hours incubation with an IC 50 of 4.5 mcg/ml. Compound IV demonstrated inhibition with IC 50 value of 1.6 mcg/ml.

Compounds II, III and IV were compared with genistein to test the cell viability of SK-MEL-28 (human malignant melanoma) cell line. Compounds II, III and IV demonstrated inhibition in SK-MEL-28 cells with IC 50 values of 3.5 µM, 5.5 µM and 3.5 µM, respectively.

Effects of Aryl Di-Substituted Propenone Compounds on the Induced Growth of Myeloma Cells.

Compound IV was compared with genistein to test the cell viability of AB1 cells (murine myeloma).

The results obtained demonstrate that genistein showed inhibition of AB1 cells at 96 hours incubation with an IC 50 of 1.1 mcg/ml. Compound IV demonstrated comparable inhibition with an IC 50 1.1 mcg/ml.

EXAMPLE 4

Activity of Compounds II and III in Respect of Hormone Related Cancers

Compounds II and III were tested in vivo for their anti-cancer activity at a range of doses in a xenograft mouse model employing human prostate cancer cells after preliminary studies showed that both compounds had demonstrated significant anti-proliferative and cytotoxic effect against a range of tumour cell lines in culture. Of the compounds, Compound II has the most anti-tumour effect. As is shown in tumour growth data in FIG. 1, treatment with Compound II caused delay in the growth of DU-145 tumours. Maximum effectiveness for this drug was seen in the group treated with a dose of 10 mg/kg which resulted in a 42% reduction mean tumour growth relative to the control group at the completion of treatment.

The cell lines were cultured and prepared for inoculation according to standard protocols.

Experimental Results

Anti-Tumour Efficacy in Xenograft Models

Female athymic mice (54) were implanted subcutaneously in the right hind flank with human DU145 prostate tumour cells ($5 \times 10^6$). Tumour formation and growth were monitored until the tumours reached an average 25 $mm^2$ area (5 mm×5 mm). Mice were randomised into groups based upon tumour area (mean tumour area in individual groups ranged from 22 $mm^2$-33 $mm^2$). Compositions of Compounds II and III were prepared in a solution of 5% DMSO, 10% Tween 80 in PBS and administered intraperitoneally in a volume of 100 µl at doses of 50, 25, and 10 mg/kg to individual eight week old female Balb/c mice for 14 days. Vehicle control was 5% DMSO, 10% Tween 80 in PBS.

Tumour growth as measured at the end of the treatment period is displayed in FIG. 2. Compound II clearly inhibited tumour growth relative to the control animals treated with vehicle alone. This inhibition was statistically significant (t-test $P<0.05$) for the 25 mg/kg and 10 mg/kg treatment groups. The overall effect was of inhibition as the tumour size in all groups continued to increase over the treatment period although growth rate was slowest in the animals treated with Compounds II.

Following the cessation of treatment all tumours continued to grow at a similar rate but treatment group tumours remained smaller in those animals treated with Compound II as is shown by growth data over the entire study period (FIG. 4). The variability of tumour growth data seen at later time points is due to declining animal numbers as tumour sizes reached 100 $mm^2$ and animals were euthanased. Compound II showed superior anti-tumour effect in comparison with Compound III.

As the most cytotoxic compound in previous cell culture testing, Compound II might have been expected to exhibit the most anti-tumour efficacy but may also have the most toxic side effects in the animal models. This was not found to be the case and overall, Compound II was better tolerated by the animals than Compound III although neither compound resulted in unacceptable toxicity at the doses used.

It is to be understood that, although prior art use and publications may be referred to herein, such reference does not constitute an admission that any of these form a part of the common general knowledge in the art, in Australia or any other country.

Numerous variations and modifications will suggest themselves to persons skilled in the relevant art, in addition to those already described, without departing from the basic inventive concepts. All such variations and modifications are to be considered within the scope of the present invention, the nature of which is to be determined from the foregoing description.

In the description of the invention, except where the context requires otherwise due to express language or necessary implication, the words "comprise" or variations such as "comprises" or "comprising" are used in an inclusive sense, i.e. to specify the presence of the stated features, but not to preclude the presence or addition of further features in various embodiments of the invention.

The invention claimed is:

1. A compound of formula (IA):

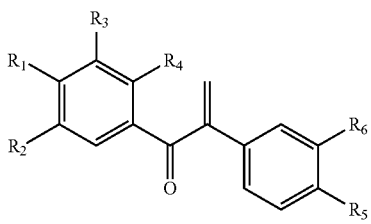

(IA)

wherein $R_1$ and $R_4$ are $OR_7$,
$R_2$ is H and $R_3$ is $OR_7$;
$R_5$ is OH or $OR_7$ and $R_6$ is H, OH or $OR_7$, with the proviso that when $R_5$ is OH, $R_6$ is not OH:
$R_7$ is alkyl, aryl or arylalkyl; or pharmaceutically acceptable salt(s) thereof,
or a compound of formula (IB):

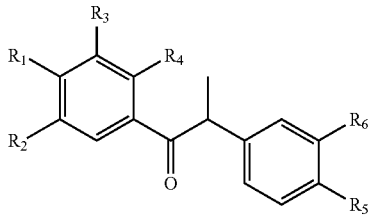

(IB)

wherein $R_1$ and $R_4$ are $OR_7$,
$R_2$ is $OR_7$ and $R_3$ is H;
$R_5$ and $R_6$ are independently H, OH or $OR_7$, with the proviso that when $R_5$ is OH, $R_6$ is not OH:
$R_7$ is aryl or arylalkyl; or pharmaceutically acceptable salt(s) thereof.

2. A compound according to claim 1 which is 1-(2,3,4-trimethoxyphenyl)-2-(4-methoxyphenyl)prop-2-en-1-one having the structure (II):

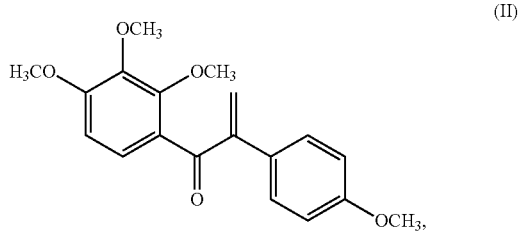 [SMILES: C=C(C(=O)c1ccc(OC)c(OC)c1OC)c1ccc(OC)cc1]

(II)

or a pharmaceutically acceptable salt or prodrug thereof.

3. A composition comprising one or more of the compounds of general formulae (IA) or (IB) as defined in claim 1, in association with one or more pharmaceutically, cosmetically or veterinarily acceptable vehicles, adjuvants, enhancers, diluents, and/or excipients.

4. A food or drink composition containing one or more of the compounds of general formulae (IA) or (IB) as defined in claim 1.

5. A method for treatment, amelioration, and/or defense against breast cancer, ovarian cancer, endometrial cancer, prostatic cancer, and/or melanoma, which method comprises administering to a subject a therapeutically effective amount of one or more of the compounds of general formulae (IA) or (IB) as defined in claim 1, either alone or in association with one or more pharmaceutically, cosmetically or veterinarily acceptable vehicles, adjuvants, enhancers, diluents, and/or excipients.

* * * * *